(12) United States Patent
El Semary

(10) Patent No.: US 11,820,974 B1
(45) Date of Patent: Nov. 21, 2023

(54) POMEGRANATE MOLASSES MEDIUM FOR CULTURING MICROBES

(71) Applicant: KING FAISAL UNIVERSITY, Al-Ahsa (SA)

(72) Inventor: Nermin Adel Hussein El Semary, Hofouf (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 17/900,130

(22) Filed: Aug. 31, 2022

(51) Int. Cl.
*C12N 1/20* (2006.01)

(52) U.S. Cl.
CPC ............ *C12N 1/20* (2013.01); *C12N 2500/24* (2013.01); *C12N 2500/42* (2013.01); *C12N 2500/76* (2013.01)

(58) Field of Classification Search
CPC . C12N 1/10; C12N 1/105; C12N 1/12; C12N 1/125; C12N 1/14; C12N 1/145; C12N 1/16; C12N 1/165; C12N 1/20; C12N 1/205; C12N 2500/76
See application file for complete search history.

(56) References Cited

FOREIGN PATENT DOCUMENTS

| CN | 103610709 A | 3/2014 |
| CN | 106045956 B | 10/2016 |
| CN | 108314559 A | 7/2018 |

OTHER PUBLICATIONS https://en.wikipedia.org/wiki/Pomegranate_molasses (Year: 2023).*
"Pomegranate Peel as Fertilizer." Ecotika F&F Website (https://ecotikaindia.online/free-ke-funde/fertilizers-made-easy/pomegranatepeel/, Downloaded Apr. 14, 2022.

* cited by examiner

*Primary Examiner* — Ruth A Davis
(74) *Attorney, Agent, or Firm* — Nath, Goldberg & Meyer; Richard C. Litman

(57) ABSTRACT

A pomegranate molasses medium for culturing microbes includes a mixture of pomegranate molasses, soil extract, and water. The pomegranate molasses medium for culturing microbes may optionally include at least one of potassium dihydrogen phosphate and iron ammonium EDTA. At least one beneficial microbe may be cultured on the pomegranate molasses medium. The at least one beneficial microbe may include, e.g., *Cyanothece* and/or beneficial fungus.

7 Claims, No Drawings

POMEGRANATE MOLASSES MEDIUM FOR CULTURING MICROBES

BACKGROUND

1. Field

The disclosure of the present patent application relates to a medium for culturing microbes and, particularly, to a pomegranate molasses medium for culturing microbes.

2. Description of the Related Art

Fertilizers are applied to soil or plant tissues to supply plant nutrients. Traditionally, fertilizers were produced from composting, animal manure, human manure, and bio-products of human industrial processes (such as fish processing waste). More recently the development of the agricultural industry resulted in a transition to synthetically created fertilizers. The use of synthetic fertilizer has resulted in significant deleterious environmental impacts, including agricultural runoff leading to ocean dead zones, waterway contamination, soil microbiome degradation, and accumulation of toxins in ecosystems.

As the negative effects of synthetic fertilizers have become more widely known, global demand for food (and thus for the use of fertilizers in agricultural processes) has only grown. Thus, recent efforts to meet this increasing demand while reducing negative environmental effects have focused on developing sustainable, regenerative agricultural practices, including the use of environmentally friendly fertilizers. However, demand for fertilizers continues to outpace the supply of organic, environmentally friendly fertilizer production.

Thus, a pomegranate molasses medium for culturing microbes is desired.

SUMMARY

A pomegranate molasses medium for culturing microbes includes a mixture of pomegranate molasses, soil extract, and water. The pomegranate molasses medium for culturing microbes may optionally include at least one of potassium dihydrogen phosphate and iron ammonium EDTA. At least one beneficial microbe may be cultured on the pomegranate molasses medium. The at least one beneficial microbe can be used in biofertilization of soil, e.g., semi-arid soils, by adding directly to the soil. In an embodiment, the at least one beneficial microbe may include e.g. *Cyanothece* (blue green alga), beneficial fungus or both. The pomegranate molasses may be obtained from pomegranate-based industrial waste and diluted (1:100, v/v).

These and other features of the pomegranate molasses medium for culturing microbes will become readily apparent upon further review of the following specification.

DETAILED DESCRIPTION OF THE PREFERRED EMBODIMENTS

A pomegranate molasses medium for culturing microbes includes a mixture of pomegranate molasses, soil extract, and water. The pomegranate molasses medium for culturing microbes may optionally include at least one of potassium dihydrogen phosphate and iron ammonium EDTA. At least one beneficial microbe may be cultured on the pomegranate molasses medium. The at least one beneficial microbe may be capable of nitrogen-fixation and photosynthesis. The at least one beneficial microbe can be used in biofertilization of soil, e.g., semi-arid soils, by adding directly to the soil. In an embodiment, the at least one beneficial microbe may include e.g. *Cyanothece* (blue green alga, beneficial fungus or both. The combination of beneficial blue-green alga and beneficial fungus can be particularly beneficial for improving crop productivity and improving soil quality. The pomegranate molasses may be obtained from pomegranate-based industrial waste.

As used herein, "pomegranate molasses" refers to a thickened syrup or juice from the pomegranate. As set forth herein, the pomegranate molasses may be produced as a byproduct during industrial processing of the pomegranate fruit.

As used herein, "about" when used to modify a numerical value means any value within 10% of the numerical value.

As used herein, "soil extract" refers to an extract obtained from a clay based, pesticide-free soil.

As used herein, "beneficial microbe" refers to any microbe that is known in the art to be desirable in the growth of agricultural products.

In an embodiment, the beneficial microbe may be mixotrophic cyanobacteria (otherwise known as blue green algae). The mixotrophic cyanobacterium may include e.g. *Cyanothece* species.

In an embodiment, a mixture of at least two beneficial microbes, including but not limited to *Cyanothece* species and fungi may be cultured on the pomegranate molasses medium.

In an embodiment, the pomegranate molasses medium may be used to culture some desired beneficial microorganism, including beneficial cyanobacteria or beneficial fungi.

In an embodiment, the pomegranate molasses medium may be used to culture a beneficial microorganism, which may be used to biofertilize a soil. The beneficial microorganism may be particularly well suited to fertilization of arid soils, or semi-arid soils. The beneficial microorganism may be a mixotrophic cyanobacterium, including but not limited to a *Cyanothece* species.

In an embodiment, the soil extract may be produced by sieving herbicide-free soil, adding water at a ratio of about 10 ml:1 g soil, stirring and filtering to obtain a filtrate. The filtrate may then be used as soil extract. In a further detailed embodiment, about 100 g of herbicide-free soil may be sieved to remove gravel, mixed with about 1000 ml of water, stirred and allowed to stand for about an hour. This soil solution may then be filtered using multiple layers of cheese cloth and the filtrate may be autoclaved and used as soil extract in the production of pomegranate molasses media. In an embodiment, about 20 ml of dilute pomegranate molasses. about 200 ml of soil extract, and about 780 ml distilled water can be combined to form a first media for culturing microbes. In an embodiment, about 20 ml of dilute pomegranate molasses, about 200 ml of soil extract, about 10 ml potassium dihydrogen phosphate (1 mM), about 10 ml iron ammonium EDTA (0.1 mM), and about 760 ml distilled water can be combined to provide a high yield media for culturing some microbes. In an embodiment, about 40 ml of dilute pomegranate molasses, about 400 ml of soil extract, about 20 ml potassium dihydrogen phosphate (1 mM), about 20 ml iron ammonium EDTA (0.1 mM), and about 520 ml distilled water can be combined to form a co-culturing media for culturing some microbes.

The present disclosure may be better understood in view of the following examples, which are illustrative only and are not intended to limit the present teachings.

Example 1

Preparation of Basic Pomegranate Molasses Media for Culturing Microbes 20 ml of dilute pomegranate molasses, 200 ml of soil extract, and 780 ml distilled water were combined to form a first media for culturing microbes. The pomegranate molasses was first mixed with the soil extract, then sufficient water was added to reach a total volume of 1 liter. The resulting media was then sterilized.

This media was particularly suited for growing *Cyanothece* species.

Example 2

Preparation of Pomegranate Molasses Media for High Yield Production 20 ml of dilute pomegranate molasses, 200 ml of soil extract, 10 ml potassium dihydrogen phosphate (1 mM), 10 ml iron ammonium EDTA (0.1 mM), and 760 ml distilled water were combined to provide a high yield media for culturing microbes. The high yield pomegranate molasses medium was made by mixing the pomegranate molasses with the soil extract to form a mixture. Then, the potassium dihydrogen phosphate (1 mM), and the iron ammonium EDTA (0.1 mM) were added to the mixture with sufficient water to reach a total volume of 1 liter. The resulting media was then sterilized.

This media was particularly suited for growing a high yield large biomass over a short period of time.

Example 3

Preparation of Pomegranate Molasses Media for Co-Culturing 40 ml of dilute pomegranate molasses, 400 ml of soil extract, 20 ml potassium dihydrogen phosphate (1 mM), 20 ml iron ammonium EDTA (0.1 mM), and 520 ml distilled water were combined to form a co-culturing media for culturing microbes. The high yield pomegranate molasses medium was made by first mixing the pomegranate molasses with the soil extract to form a mixture. Then, potassium dihydrogen phosphate (1 mM) and iron ammonium EDTA (0.1 mM) were added to the mixture with sufficient water to reach a total volume of 1 liter. The resulting media was then sterilized.

This media was particularly suited for co-culturing multiple beneficial microbes of interest, including by non-limiting example culturing a *Cyanothece* sp. with another beneficial microbe or co-culturing a *Cyanothece* sp. with a second, distinct *Cyanothece* species. This media is also well suited to growing a high yield large biomass over a short period of time.

It is to be understood that the pomegranate molasses medium for culturing microbes is not limited to the specific embodiments described above but encompasses different embodiments within the scope of the generic language of the following claims enabled by the embodiments described herein, or otherwise shown in the drawings or described above in terms sufficient to enable one of ordinary skill in the art to make and use the claimed subject matter.

I claim:

1. A pomegranate molasses medium for culturing microbes, comprising:
   about 20 ml pomegranate molasses diluted with water in a 1:100 v/v/ratio;
   about 200 ml soil extract, wherein the soil extract is produced by sieving an herbicide-free soil, adding water at a ratio of 10 ml water:1 g of soil, stirring and filtering to obtain a filtrate used as the soil extract; and
   about 780 ml distilled water.

2. The pomegranate molasses medium for culturing microbes of claim 1, further comprising at least one additional ingredient selected from the group consisting of potassium dihydrogen phosphate and iron ammonium EDTA.

3. The pomegranate molasses medium for culturing microbes of claim 2, wherein the pomegranate molasses medium comprises:
   about 20 ml of the pomegranate molasses diluted with water in a 1:100 v/v/ratio;
   about 200 ml of the soil extract;
   about 10 ml of the potassium dihydrogen phosphate having a molar concentration of 1 mM;
   about 10 ml of the iron ammonium EDTA having a molar concentration of 0.1 mM; and
   about 760 ml of the distilled water.

4. The pomegranate molasses medium for culturing microbes of claim 2, wherein the pomegranate molasses medium comprises:
   about 40 ml of the pomegranate molasses diluted with water in a 1:100 v/v/ratio;
   about 400 ml of the soil extract;
   about 20 ml of the potassium dihydrogen phosphate having a molar concentration of 1 mM;
   about 20 ml of the iron ammonium EDTA having a molar concentration of 0.1 mM; and
   about 520 ml of the distilled water.

5. A method of culturing at least one beneficial microbe, the method comprising:
   providing the pomegranate molasses medium for culturing microbes of claim 1; and
   culturing the at least one beneficial microbe on the pomegranate molasses medium,
   wherein the soil extract in the pomegranate molasses medium for culturing microbes is produced by sieving an herbicide-free soil, adding water at a ratio of 10 ml water:1 g of soil, stirring and filtering to obtain a filtrate used as the soil extract.

6. The method of culturing at least one beneficial microbe of claim 5, wherein the at least one beneficial microbe comprises at least one of a first beneficial microbe and a second beneficial microbe.

7. The method of culturing at least one beneficial microbe of claim 5, wherein the at least one beneficial microbe is selected from the group consisting of a mixotrophic cyanobacteria, fungi, and combinations thereof.

* * * * *